US00PP13395P3

(12) United States Plant Patent
Fear et al.

(10) Patent No.: US PP13,395 P3
(45) Date of Patent: Dec. 24, 2002

(54) PLUM TREE NAMED 'SUPLUMTWENTYFOUR'

(75) Inventors: Carlos D. Fear, Aptos; Bruce D. Mowrey, La Selva Beach; David W. Cain, Bakersfield, all of CA (US)

(73) Assignee: Sun World International, Inc., Bakersfield, CA (US)

( * ) Notice: Subject to any disclaimer, the term of this patent is extended or adjusted under 35 U.S.C. 154(b) by 13 days.

(21) Appl. No.: 09/792,860

(22) Filed: Feb. 23, 2001

(65) Prior Publication Data

US 2002/0152520 P1 Oct. 17, 2002

(51) Int. Cl.[7] ..... A01H 5/00

(52) U.S. Cl. ..... Plt./184

(58) Field of Search ..... Plt./184

*Primary Examiner*—Bruce R. Campell
*Assistant Examiner*—Susan B. McCormick

(57) ABSTRACT

A new and distinct plum variety that has mildly sweet fruit, black skin, and bright red flesh with abundant juice is described. The new variety has consistently high productivity, setting crops even in rainy, cool bloom conditions.

1 Drawing Sheet

LATIN NAME OF THE GENUS AND SPECIES OF THE PLANT CLAIMED

*Prunus salicina.*

VARIETY DENOMINATION

'Suplumtwentyfour'.

BACKGROUND AND SUMMARY OF THE INVENTION

This invention relates to the discovery and asexual propagation of a new variety of plum, *Prunus salicina* cv. 'Suplumtwentyfour'. The new variety was first hybridized by Carlos D. Fear and selected by Bruce D. Mowrey. The new variety was evaluated by Bruce D. Mowrey and David W. Cain near Wasco, Kern County, Calif. The variety was originated by hybridization. The new variety is characterized by its high consistent productivity, setting crops even in rainy, cool bloom conditions.

The seed parent is 'Suplumtwelve' (U.S. Plant Pat. No. 4,965) and the pollen parent is Sun World breeding selection '275-136' (unpatented). The parent varieties were first crossed in 1988, with the date of sowing of March 1989 and the date of first flowering being 1991. The new plum variety was first asexually propagated by Bruce D. Mowry near Wasco, Kern County, Calif. in May 1992, by budding onto Nemared rootstock.

The new variety 'Suplumtwentyfour' is similar to its seed parent the 'Suplumtwelve' variety in that it has approximately the same ripening date. It differs from its seed parent by having flesh that is more nearly solid, bright red color. The seed parent, in contrast, is more yellow in color in the region near the pit cavity until the fruit is at the soft ripe stage. 'Suplumtwentyfour' may be further distinguished from its seed parent by having larger size fruits, (averaging 7.0 cm in diameter compared to 6.3 cm for 'Suplumtwelve'), a rounder, less oblate shape, and a smoother skin surface as compared to the more corrugated skin surface texture of the seed parent 'Suplumtwelve'.

The new 'Suplumtwentyfour' variety is distinguished from its pollen parent '275-136' (unpatented) by yielding larger fruits, averaging 7.0 cm. in diameter compared to the 6.0 cm fruits of '275-136'. Fruits of 'Suplumtwentyfour' are rounder as compared to the more oblate shape of '275-136' fruits. The flesh of 'Suplumtwentyfour' is brighter and more nearly solid red, developing earlier than in '275-136', which has a more yellow flesh in the pit region until the fruit is fully ripe. The new variety is more consistently productive than '275-136', setting full crops in rainy, cool bloom conditions while '275-136' sets poorly under such conditions. The new variety ripens approximately nine days after its pollen parent '275-136'.

The new plum variety cv. 'Suplumtwentyfour' most nearly resembles the 'Suplumeleven' (U.S. Plant Pat. No. 4,902) variety. It may be distinguished from the 'Suplumeleven' by having more intense red flesh coloration which develops earlier in the maturation process than 'Suplumeleven'. 'Suplumtwentyfour' ripens approximately 20 days earlier than 'Suplumeleven', with fruit that is softer, with more melting flesh texture than in the 'Suplumeleven' variety. Moreover, the fruit of 'Suplumtwentyfour' is more nearly round and less oblate in shape than 'Suplumeleven'.

The new 'Suplumtwentyfour' variety vaguely resembles the 'Black Amber' variety, but differs from 'Black Amber' by producing fruit with red-colored flesh in contrast to the yellow flesh of the 'Black Amber' variety. The new variety yields larger fruits that are more uniform in comparison to the 'Black Amber' variety. Additionally, the 'Suplumtwentyfour' variety ripens approximately five days earlier than the 'Black Amber' variety.

The new variety 'Suplumtwentyfour' ripens at the same time as the 'Santa Rosa' plum variety. It differs from the 'Santa Rosa' variety by possessing black skin and bright red flesh, in comparison to the dark red skin and yellow-red flesh of the 'Santa Rosa' variety.

The new 'Suplumtwentyfour' variety has been shown to maintain its distinguishing characteristics through successive asexual propagations by, for example, budding onto 'Nemared' rootstock.

BRIEF DESCRIPTION OF THE FIGURE

The accompanying drawing in FIG. 1 illustrates in full color.

DETAILED BOTANICAL DESCRIPTION OF THE INVENTION

Figure 1:
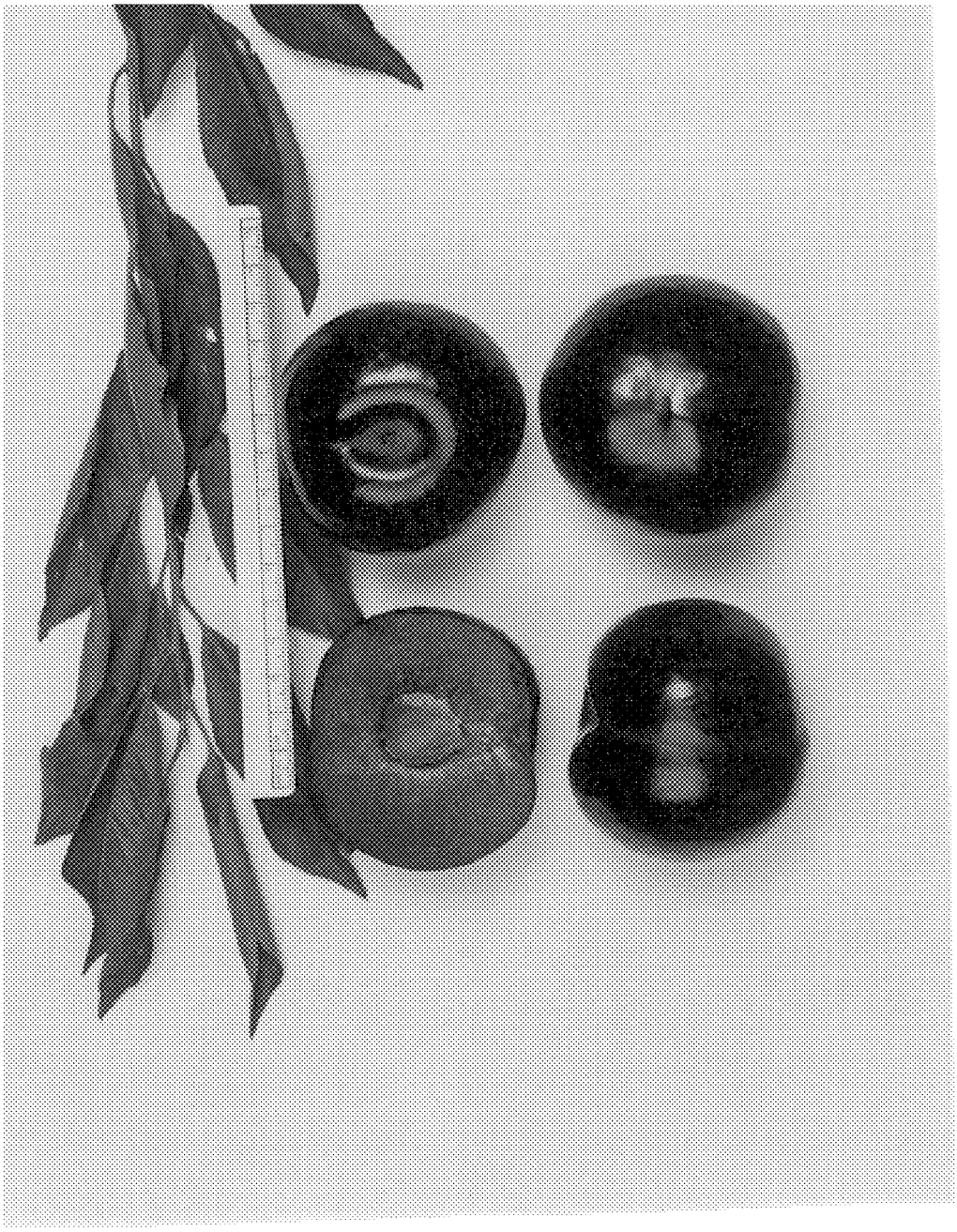

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

The descriptive matter which follows pertains to 11 year old 'Suplumtwentyfour' plants grown in the vicinity of Wasco, Kern County, during 2000, and is believed to apply to plants of the variety grown under similar conditions of soil and climate elsewhere:

TREE

General:
- *Height of tree.*—Reduced by pruning to approximately 300 to 400 cm in height and maintained at about 250 cm wide. Vigor: vigorous. shoot growth rate is about 45 to 100 cm in one year on a mature tree (Growth rate is affected by cultural and environmental factors).
- *Habit.*—Semi-upright.
- *Density of foliage.*—Medium.
- *Shape.*—Vase formed.
- *Hardiness.*—Hardy under central California conditions.
- *Productivity.*—Very productive.
- *Fruit bearing.*—Regular bearer.
- *Root stock.*—Nemared.

Trunk:
- *Shape.*—Round.
- *Diameter at about 30 cm above soil level.*—About 20 cm.
- *Texture.*—Medium shaggy; varies with age.
- *Color.*—About 200 D.

Branches:
- *Shape.*—Round.
- *Diameter at 70 cm above the soil line.*—About 7 cm to 9 cm.
- *Surface texture.*—Medium shaggy.
- *Color.*—About 166B to about 200C.
- *Surface appearance.*—Dull.

Lenticels:
- *Number.*—Medium.
- *Diameter.*—About 0.8 mm.
- *Color.*—About 156B.

LEAVES

General:
- *Average length.*—About 10.1 cm.
- *Average width.*—About 3.5 cm.
- *Size.*—Large.
- *Outline.*—Elliptic.
- *Profile.*—Up folded.
- *Leaf blade tip.*—Curved downwardly slightly.
- *Angle of tip.*—Acute.
- *Margin.*—Crenate.
- *Undulation of margin.*—Slight.
- *Apex.*—Acuminate.
- *Base.*—Cuneate.
- *Thickness.*—Medium.
- *Venation pattern.*—Pinnate.
- *Vein color.*—144B.

Upper surface:
- *Color.*—About 137A.
- *Glossiness.*—Medium.
- *Pubescense.*—Absent.
- *Surface texture.*—Smooth.
- *Surface appearance.*—Semi-glossy.

Lower surface:
- *Color.*—About 137C.
- *Glossiness.*—Weak.
- *Pubescense.*—Absent.
- *Surface texture.*—Smooth.
- *Surface appearance.*—Dull.

Petiole:
- *Length.*—Medium, about 1.1 cm.
- *Thickness.*—Medium, about 2 mm.
- *Color.*—About 144A, with highlights of red 47B.

Glands:
- *Average number.*—4.
- *Positioning.*—(a) On petiole; (b) Opposite.
- *Size.*—Small, about 1 mm.
- *Shape.*—Globose.
- *Color.*—About Green 139D.

Stipules:
- *Persistence.*—Persistent.

Wood (leaf) buds:
- *Shape.*—Conical.
- *Size (on a typical flowering shoot of about 5 mm in diameter.*—About 2 mm wide at widest point, by about 2.5 mm long.
- *Position relative to shoot.*—Slightly. — held out.
- *Support.*—Not decurrent.
- *Time of bud burst.*—Occurs at about first bloom date.

Flowering shoots:
- *Anthocyanin coloration.*—Absent.
- *Intensity.*—Medium.
- *Thickness.*—Medium, about 0.4 cm.
- *Internode length.*—Medium, about 2.6 cm.
- *Density of buds.*—Medium.
- *Distribution.*—Isolated in groups of 2 or more on spurs and one year old shoots.
- *Ratio of wood (leaf) buds to flowering shoots.*—Ranging from 1:4 to 1:16.

FLOWERS

Flower-buds:
- *Hardiness.*—Hardy under California conditions.
- *Size on a typical flowering shoot of about 5 mm in diameter.*—About 3 mm wide at widest point by about 3.5 mm long.
- *Length.*—Medium.
- *Shape.*—Ovoid.
- *Positioning.*—Free.
- *Pubescence.*—Absent.
- *Color.*—About 177A.

General:
- *Date of first bloom.*—Feb. 20, 2000.
- *Date of full bloom.*—Feb. 25, 2000.
- *Time of bloom.*—Medium, as compared with similar varieties in the growing area of Wasco, Kern County, Calif.

*Duration of bloom.*—Medium, about 10 days.
*Size* (*diameter of the fully open flower*).—Medium, about 2.2 cm.
*Shape.*—Rosaceous.
*Petals.*—Free.
*Color* (*fully opened flower*).—White.

Peduncle:
*Diameter.*—About 0.9 mm.
*Color.*—About 145A.
*Length.*—0.8 mm.
*Pubescence.*—Absent.

Receptacle:
*Depth.*—Medium.
*Pubescence of inner surface* (*at white bud stage*).—Absent.
*Pubescence of outer surface.*—Absent.

Sepals:
*Positioning.*—Adpressed to petals.
*Shape.*—Elliptic.
*Color.*—About 145A.
*Width.*—About 2 mm at widest point.
*Length.*—About 2.5 mm long.
*Pubescence of inner surface.*—Absent.
*Pubescence of outer surface.*—Absent.
*Frequency of flowers with double sepals.*—None.

Petals:
*Frequency of flowers with double petals.*—None.
*Width.*—Medium, about 0.6 cm.
*Length.*—About 1 cm.
*Shape.*—Transverse broad elliptic.
*Shape of apex.*—Rounded.
*Claw length.*—Short.
*Margin waviness.*—Medium.
*Shape of base.*—Petal narrows as it nears the base.
*Base angle.*—Medium.
*Division of upper margin.*—Entire.
*Pubescence of inner surface.*—Absent.
*Pubescence of outer surface.*—Absent.
*Color* (*inner surface*).—White.
*Color* (*outer surface*).—White.

Stigma:
*Position* (*as compared with anthers*).—Below.

Anthers:
*Color* (*just before dehiscence*).—About Yellow 23C, with slight shadings of about red 45D.

Pollen:
*Color.*—About 14D.

Stamens:
*Position.*—Perigynous.

Pistil:
*Length at full bloom.*—About 7 mm.
*Frequency of supplementary pistils.*—Absent.
*Number.*—Always one.

Ovary:
*Length.*—About 0.9 mm.
*Color.*—About 143A.
*Pubescence.*—Absent.

Style:
*Shape.*—Slender.
*Color.*—About 145B.
*Pubescence* (*of base*).—Absent.

FRUIT

General:
*Maturity when described.*—Firm-ripe.
*Date.*—Jun. 19, 2000.
*Uniformity.*—Uniform.
*Size.*—Large; about 145 g.
*Length from stem to apex.*—About 6.5 cm.
*Diameter in line with suture plane.*—About 7.0 cm.
*Diameter perpendicular to suture plane.*—About 7.0 cm.
*Form.*—Rounded.
*Position of maximum diameter.*—Middle towards.
*Symmetry about the suture.*—Nearly symmetric.
*Season ripening.*—Early.
*Use.*—Fresh market.
*Keeping quality.*—Good.
*Resistance to.*—Insects: medium; typical of Japanese plums. Diseases: medium; typical of Japanese plums. Shipping quality: Good. Fruit stored for 3 weeks at 38° F. to 42° F. showed no internal browning or mealiness of flesh.

Suture: An inconspicuous line that is shallow and extends from base to apex.

Ventral surface:
*Shape.*—Rounded slightly.
*Lips.*—Equal.
*Depression of apex.*—Distinct.
*Pistil base.*—Not persisting.
*Pubescence at apex.*—Absent.
*Density of apex pubescence.*—Absent.

Stem cavity:
*Shape.*—Rounded and flaring.
*Depth.*—About 1.5 cm.
*Breadth.*—About 2.1 cm.
*Markings.*—None.

Base:
*Shape.*—Rounded.

Apex:
*Shape.*—Slightly depressed.

Pistil point:
*Shape.*—Oblique.

Stem:
*Length.*—Medium, about 0.88 cm.
*Color.*—About 143C.
*Adherence to stone.*—Stem adheres to stone moderately but separates from the stone more readily than from the tree.

Skin:
*Thickness.*—Medium.
*Texture at harvest.*—Smooth and crisp.
*Reticulation.*—Absent.
*Roughness.*—Absent.
*Taste.*—Tart.
*Tenacity.*—Tenacious to flesh.
*Tendency to crack.*—None in wet season.
*Color.*—About Greyed-Purple 187A, becoming black when ripe.
*Down* (*pubescence*) None.
*Bloom.*—Present.

Flesh:
*Color.*—About Red 46A.
*Surface of the pit cavity.*—About 46A when ripe.
*Amygdalin.*—Wanting.
*Juice.*—Abundant.
*Sugar content.*—Medium (about 14–15% SS).
*Texture.*—Medium; fine; melting.
*Fibres.*—Few.
*Ripens.*—Even.
*Flavor.*—Mildly sweet.
*Aroma.*—Wanting.

*Eating quality.*—Good.
*Stone/flesh ratio.*—1.3 cm: 7 cm.

STONE

General:
*Adherence to flesh.*—Semi-free.
*Fibres.*—Retains short fiber.
*Size.*—Medium.
*Length.*—About 2.2 cm.
*Breadth.*—About 1.9 cm.
*Width of stalk end.*—About 0.3 cm.
*Angle of stalk end.*—Right angle.
*Thickness.*—About 1.1 cm.
*Form* (*profile*).—Globose.
*Form* (*ventral view*).—Flattened.
*Base.*—Nearly straight.
*Hilum.*—Oblong.
*Apex.*—Rounded with a small, sharp point.
*Position of maximum breadth.*—Middle.
*Sides.*—Equal.
*Surface.*—ridged.
*Outgrowing keel.*—Partly developed.
*Ridges.*—Jagged.
*Pits.*—Angular.
*Ventrical edge.*—Thin with wing toward base and extending throughout.
*Dorsal edge.*—Medium thickness, with shallow groove throughout.
*Color of stone.*—About Greyed-Orange 164C.
*Tendency to split.*—None.
*Kernel length* (*when dried*).—About 15 mm.
*Kernel diameter in line with suture plane* (*when dried*).—About 9 mm.
*Kernel diameter perpendicular to suture plane* (*when dried*).—About 4 mm.
*Kernel astringency.*—Bitter.
*Kernel shape.*—Oval.
*Kernel viability.*—Viable.

Suplumtwentyfour: Table of R.H.S. Color Codes:

| | | R.H.S. Color Code |
|---|---|---|
| LEAVES: | | |
| Upper Surface: | | 137A |
| Lower Surface: | | 137C |
| Glands: | | 139D |
| FLOWERS: | | |
| Flower Buds: | | 177A |
| Anthers: | Just before dehiscence: | 23C with slight shadings of 45D |
| Pollen: | | 14D |
| FRUIT: | | |
| Skin: | | 187A (becoming black when ripe) |
| Flesh: | | 46A |
| | Surface of the pit cavity when ripe: | 46A |
| STONE: | | |
| | Stone color: | 164C |

What is claimed is:

1. A new and distinct plum tree as herein described and illustrated.

* * * * *